US005765563A

United States Patent [19]
Vander Schaaf

[11] Patent Number: 5,765,563
[45] Date of Patent: Jun. 16, 1998

[54] PATIENT MONITORING SYSTEM

[75] Inventor: Larry Allen Vander Schaaf, Hastings, Minn.

[73] Assignee: Nellcor Puritan Bennett Incorporated, Pleasanton, Calif.

[21] Appl. No.: 698,137

[22] Filed: Aug. 15, 1996

[51] Int. Cl.$^6$ .................................. A61B 5/08
[52] U.S. Cl. ............... 128/725; 128/724; 128/700; 128/671
[58] Field of Search ................ 128/633, 716, 128/719, 725, 724, 700, 666, 668, 670, 671

[56] References Cited

U.S. PATENT DOCUMENTS 4,999,772  3/1991  Bowman et al. ............... 128/711 X
5,275,159  1/1994  Griebel ........................... 128/716 X
5,520,176  5/1996  Cohen ............................ 128/671 X
5,546,952  8/1996  Erickson ........................ 128/716
5,555,891  9/1996  Eisenfeld ...................... 128/721
5,605,151  2/1997  Lynn ............................. 128/716 X

*Primary Examiner*—Jeffrey R. Jastrzab
*Attorney, Agent, or Firm*—Nawrocki, Rooney & Sivertson

[57] ABSTRACT

A method and apparatus for performing scoring analysis of the pathological sleep events of apnea, hypopnea and desaturation of a patient from a sampled data set of only three sensor signals, namely, airflow, heart rate and oxygen saturation. The data source is either currently sensed data or previously recorded data. A microprocessor provides the display, printing, input and output channels, operator interface and computation capability for the system. Specialized programs direct the analysis and operation thereof.

26 Claims, 12 Drawing Sheets

*Fig.9*

| PATIENT INFORMATION |

PATIENT INFORMATION
LAST NAME
FIRST NAME
BIRTH DATE           AGE
PATIENT ID#          SEX

OK
CANCEL
HELP
SAVE AS DEFAULT
LOAD DEFAULT

STUDY INFORMATION
INDICATION           COMMENTS
REVIEWED BY

INSTITUTION, INFORMATION
INSTITUTION          ADDRESS
REFERRED BY

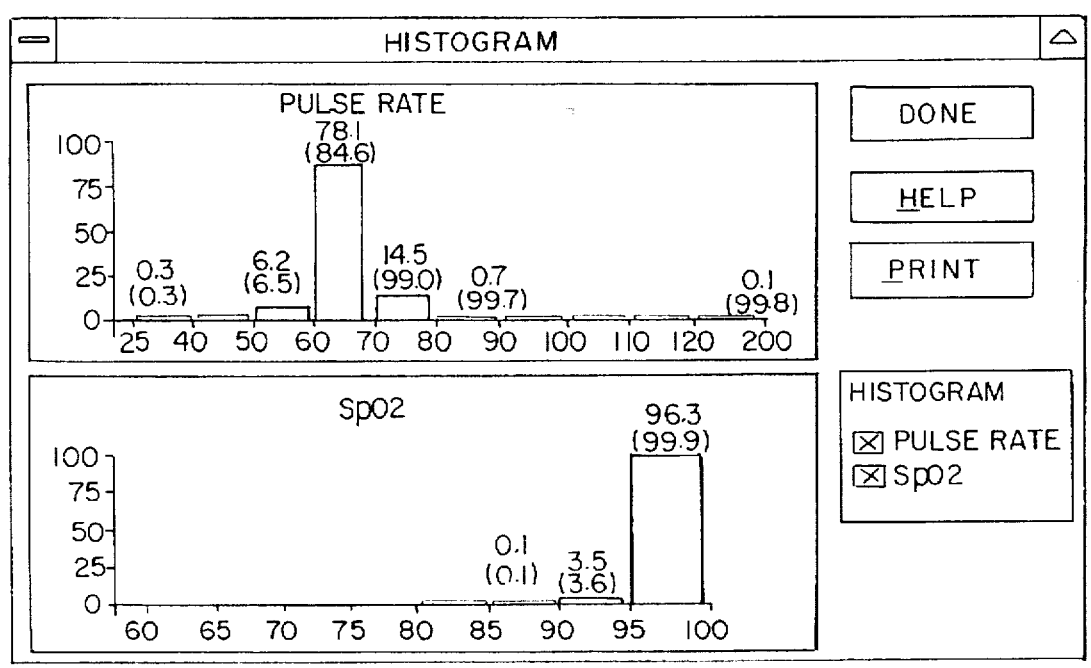

PATIENT MONITORING SYSTEM

This application is related to U.S. Pat. No. 4,621,643, issued to New, Jr. et al., and U.S. Pat. No. 5,161,541, issued to Bowman et al., both assigned to the assignee of the present invention, and both incorporated herein by reference.

BACKGROUND OF THE INVENTION

1. Field of the Invention

This invention relates to cardio respiratory monitoring and analysis and more particularly to cardio respiratory monitoring for analyzing and scoring of sleep events.

2. Description of the Prior Art

Diagnosis and treatment of sleeping disorders has improved greatly in recent years. A common method for diagnosing many sleeping disorders is to monitor a number of physiological signals of a patient, while the patient is sleeping. Since the precise time that abnormal sleep events occur is typically unknown, the clinician must monitor the number of physiological signals for an extended period of time, such as overnight. Typical signals that may be monitored to study and classify sleeping disorders include electroencephalo-grams (EEG), electrooculorgrams (EOG), electromyograms (EMG), heart rate, respiration, and oxygen saturation.

For several decades, the recordings of physiological signals was provided on long strips of paper. The clinician then examined the paper records and "scored" each sleep event that occurred. That is, the clinician typically identified and classified each sleep event manually. While this method may provide a way to identify and classify sleep events, it is readily apparent that it may be time consuming and susceptible to error. Further, because the analysis was so time consuming, the economic feasibility of diagnosing sleeping disorders was limited, except in the most extreme cases.

With the advent of physiological recorders, the effective diagnosis of sleeping disorders has become more widespread. Physiological recorders are devices that may be used to electronically record physiological signals over a long period of time, such as overnight.

A number of computer systems have been developed to perform statistical and spectral analysis on the electronically stored physiological signals. One such system is described in U.S. Pat. No. 5,291,400, issued to Gilham. Gilham suggests a system for analyzing heart variability. In Gilham, a computer system generates various statistical and spectral data corresponding to heart rate variability, including power spectra, and displays the results.

Another such system is suggested in U.S. Pat. No. 5,274,548, issued to Bernard et al. Bernard et al. suggest a method for automatic analysis of signals by segmenting the physiological signal and performing classification thereon. The signals are segmented by aggregating samples and merging adjacent pulses before analysis.

U.S. Pat. No. 5,299,118, issued to Martens et al., discloses an analysis system that automatically classifies sleep events using a pre-programmed knowledge base. That is, Martens et al. suggests extracting features from the digitized signal data, and then attempts to match the extracted features to pre-programmed patterns within the knowledge base. The matched features are then used to classify the state of the physiological function (such as the stage of sleep) for each time period. After this analysis, the user may reclassify the event off-line by changing the patterns by which the features are matched and the classification criteria.

A limitation of all of these prior art systems is that the clinician is separated from the actual physiological data and thus removed from the actual diagnosis function. In Gilham, Bernard et al., and Martens et al., complex statistical and/or sophisticated data processing techniques are used to provide a result. However, these complex statistical and/or sophisticated data processing techniques may prevent the clinician from using his or her own expertise in making a diagnosis, because the true nature of the data may be masked thereby. Further, in Martens et al., the computer system attempts to classify each sleep event using a pre-programmed knowledge base, and appears only to allow the clinician to adjust the patterns by which the extracted features are matched and corresponding classification criteria. Finally, to properly classify sleep events, it appears Martens et al. requires a relatively large number of sensors, including respiration sensors for detecting the amplitude and frequency of respiration, movement sensors for detecting movement of the phase angle between the rib cage and abdomen, sensors for detecting intercostal EMG, and position sensors for detecting the position of the body.

Accordingly, it would be desirable to have a system that uses a comparatively small number of sensor devices and performs a comparatively simple algorithm to detect sleep events, while providing the user with the flexibility to modify the parameters used thereby, and to use his or her expertise in making a diagnosis. An automatic scoring scheme of this type would reduce the operator's load and ensure that the same repeatable criteria are used throughout the entire period, while allowing the clinician to use his or her own expertise in making a proper diagnosis. Thus, this may improve the cost effectiveness and overall efficiency of the system, while allowing a more reliable diagnosis.

SUMMARY OF THE INVENTION

The present invention provides a method and apparatus for performing scoring analysis of pathological sleep events including apnea, hypopnea and desaturation of a patient from a sampled data set of only two sensor signals, namely, airflow and oxygen saturation. Further, the present invention utilizes a comparatively simple algorithm to identify sleep events from the digitized data of the sensors. Finally, the present invention provides the user with the flexibility to selectively view the raw digitized sensor data, and modify the parameters used by the system, such that the user's expertise may be more effectively used in making a diagnosis.

In an exemplary embodiment, a system is provided for analyzing patient airflow to determine and score abnormal sleep events, and in particular apnea events. The system may have an input means, clock means, receiving means, and determining means. The input means may receive a time varying analog airflow signal from at least one sensor that is sensing the airflow of a patient, wherein the analog airflow signal corresponds to the respiration of the patient. The input means may further digitize the analog airflow signal to provide a digitized airflow signal. The clock means may provide a digital clock signal to correlate the digitized airflow signal with time. The receiving means may receive the digitized airflow signal and the digital clock signal. Finally, the determining means may determine the respiration of the patient from the digitized airflow signal, and determine a delay in the respiration of the patient, thereby indicating an apnea event.

It is contemplated that the present invention may operate in real time or may electronically store the digitized data for later analysis. That is, it is contemplated that the determining means may directly receive the digitized signals and perform processing thereon in real time. Alternatively, it is contemplated that a storing means may be provided for storing the digitized airflow signal and the digital clock signal for later display and analysis.

In another exemplary embodiment of the present invention, the digitized airflow signal may have a number of successive portions that correspond to a number of start of inspiration portions, peak of inspiration portions, start of expiration portions, and end of expiration portions. The determining means may determine the portions of the digitized airflow signal that correspond to the successive peak of inspiration portions and the corresponding successive start of inspiration portions of the digitized airflow signal. In addition, an apnea interval may be defined as the time interval between a valid peak of inspiration portion and the next succeeding start of inspiration portion. Accordingly, the determining means may determine which of the number of apnea intervals are longer than a predetermined apnea threshold, thereby indicating an apnea event.

An exemplary algorithm for determining the above referenced apnea interval recognizes that the digitized airflow signal has a number of local maximums and local minimums wherein each of the number of local maximums and local minimums have a corresponding amplitude. Some of the local maximums are valid, while others are due to non-monatomic breathing or noise. Thus, each of the number of peak of inspiration portions corresponds to one of the number of local maximums, but not necessarily vice-versa. It is contemplated that the determining means may determine which of the number of peak of inspiration portions are valid.

In a preferred embodiment, the determining means determines that a particular peak of inspiration portion is valid if: (1) the amplitude of the local maximum exceeds the amplitude of the subsequent local minimum by a predetermined threshold value; and (2) the amplitude of the local maximum drops by a predetermined amount within a predetermined time period. This time period can be defined as the average of the highest 10 of the previous 50 valid time periods or a minimum value of 1.4 seconds, whichever is greater. A time period can be measured from the local maximum to the subsequent local minimum. If both of these criteria are satisfied, the local maximum is deemed to be valid.

To further improve the detection of apnea events, the system may include a drop queue which may store a number of valid drop distances. A valid drop distance may be defined as the difference in amplitude of the digitized airflow signal from a valid peak of inspiration portion to a next succeeding end of expiration portion. The drop queue may store, in a FIFO manner, the "N" most recent valid drop distances. The drop queue may be used to determine a baseline amplitude for calculating a valid peak of inspiration. That is, the predetermined threshold value used to determine if a peak of inspiration is valid may be set to a percentage of a baseline amplitude. The baseline amplitude can be defined as the average of the second through the sixth highest valid drops in a drop queue of size 10. The highest valid drop is removed to eliminate breaths which may be atypical of the normal breathing pattern (i.e., a large sigh). The lowest breaths are removed to eliminate the effect of abnormal breathing patterns on the baseline and thereby being able to continue to detect an abnormal breathing pattern (i.e., hypopnea). The use of a baseline amplitude to calculate the predetermined threshold value, essentially provides a moving average reference level. This may yield more consistent results in situations where long term fluctuations occur—for example, those caused by a degrading signals over time.

It is contemplated that the valid drop distance must be greater than a predetermined minimum threshold before the valid drop distance is stored in the drop queue. This may prevent the predetermined threshold value from becoming too small to reject noise or other interference, thereby further assuring that the corresponding peak of inspiration is in fact a valid peak of inspiration.

For detecting hypopnea, the above referenced system may set the predetermined amount that the particular peak of inspiration portion must drop within the previously described predetermined time period, to a percentage of the predetermined threshold value discussed above. Optionally, the system may include an oxygen sensor coupled to the patient for providing a time varying oxygen saturation signal to the input means thereby resulting in a digitized oxygen saturation signal. The determining means may determine if the oxygen saturation level falls below a predetermined oxygen saturation level for a predetermined time period. If an apnea event is detected under these conditions, and optionally if the oxygen saturation level drops below the predetermined oxygen level for the predetermined time period, a hypopnea event is detected.

For desaturation detection, a fixed oxygen saturation threshold may be selected or a relative oxygen saturation threshold may be selected, or both. If the fixed oxygen saturation threshold option is selected, the system may determine if the oxygen saturation level drops below a fixed predetermined oxygen saturation threshold. If the relative oxygen saturation threshold option is selected, the system may determine if the oxygen saturation level drops below a relative oxygen saturation threshold. If both the fixed and relative oxygen saturation levels are selected, a desaturation event is detected if either test is satisfied.

It is contemplated that the relative oxygen saturation threshold may be defined as a percentage of a baseline oxygen saturation threshold. The baseline oxygen saturation threshold may be defined as follows. A baseline time interval (for example, five minutes) may be broken into "N" time windows, and an average oxygen level may be computed for each time window. The baseline oxygen saturation threshold may then be computed by averaging the highest "M" average oxygen levels for each of the "N" time windows, wherein M is less than N. To prohibit invalid signals from effecting the results, it is contemplated that any time window that has an invalid oxygen level therein may not be selected as one of the highest M oxygen levels.

Finally, it is contemplated that the above referenced system may include a pulse sensor coupled to the patient for providing a time varying heart pulse signal to the input means thereby resulting in a digitized pulse signal. The determining means may determine the pulse rate of the patient, and correlate the pulse rate with the respiration and oxygen saturation signals. This may help a clinician diagnose sleep events.

In all of the above referenced embodiments, it is contemplated that the determining means may be a digital processor. Preferably, the determining means may be a standard personal computer, which is programmed to perform the above referenced functions. Further, the standard personal computer may be programmed to provide the clinician with the flexibility to modify the parameters used by the system, and display the raw digitized sensor data, thus allowing the clinician to use his or her expertise in making a diagnosis.

BRIEF DESCRIPTION OF THE DRAWINGS

Objects of the present invention and many of the attendant advantages of the present invention will be readily appreated as the same becomes better understood by reference to the following detailed description when considered in connection with the accompanying drawings, in which like reference numerals designate like parts throughout the figures thereof, and wherein:

FIG. 9 shows an exemplary Patient Information menu in accordance with the present invention;

FIG. 14 shows an exemplary Change Time Interval menu in accordance with the present invention;

FIG. 15 shows an exemplary Histogram display including pulse rate and oxygen saturation;

DETAILED DESCRIPTION OF THE PREFERRED EMBODIMENTS

Figure 1:
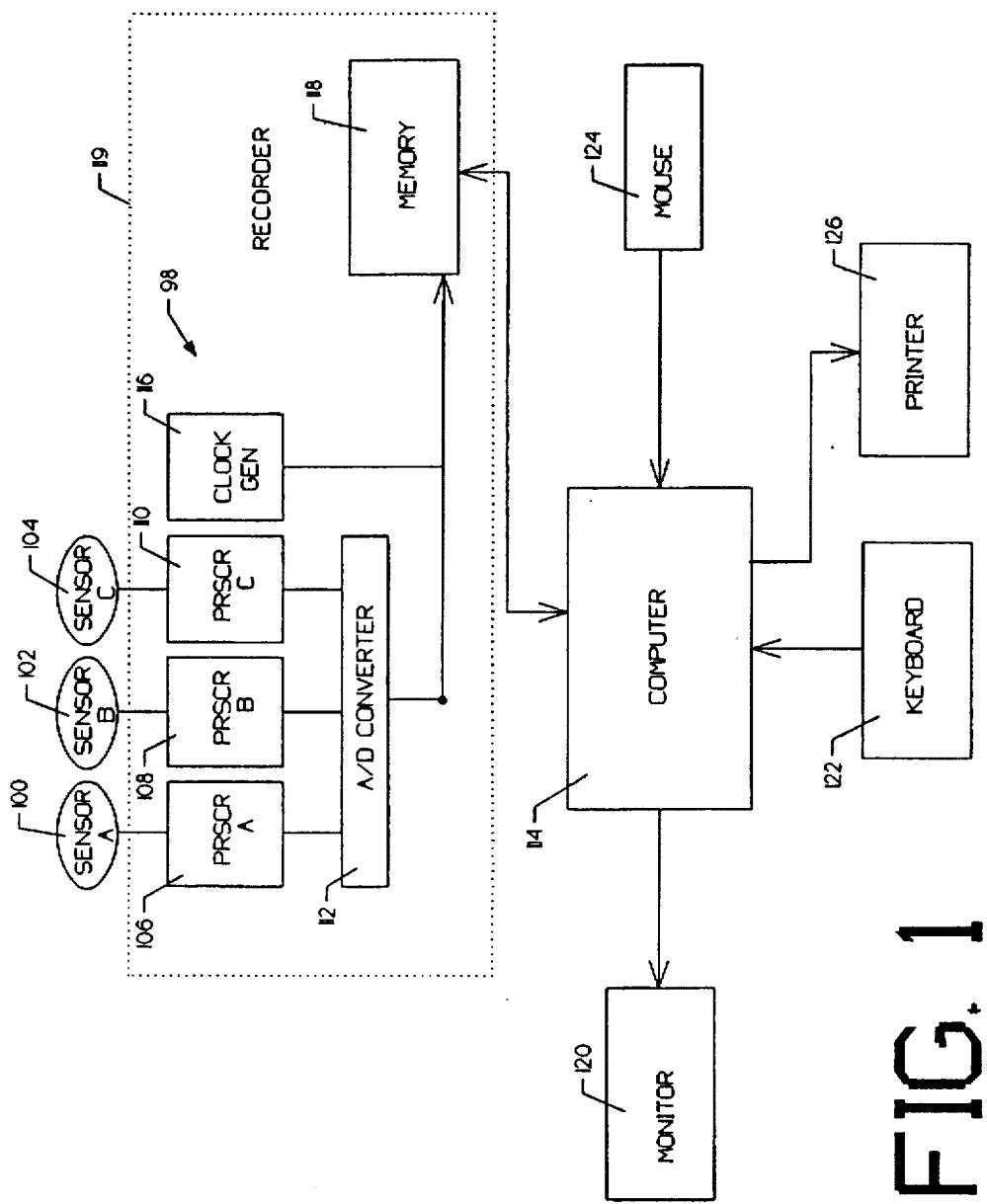
FIG. 1 is a block diagram of an exemplary embodiment of the present invention.

FIG. 1 is a block diagram of an exemplary embodiment of the present invention. The overall apparatus is shown at 98. A number of sensors are provided for detecting various physiological signal. In the exemplary embodiment shown, heart rate sensor 100, oxygen saturation sensor 102, and airflow sensor 104 are provided. In a preferred embodiment, heart rate sensor 100 and oxygen saturation sensor 102 are obtained from a combined sensor which is attached to a digit of patient 200. The combined sensor may be in accordance with New, Jr. et al. U.S. Pat. No. 4,621,643, or a similar apparatus. Airflow sensor 104 may be in accordance with Bowman et al., U.S. Pat. No. 5,161,541, which provides an analog signal corresponding to the temperature of the air passing thereover to indicated inspiration or expiration of the patient. Alternatively, airflow sensor 104 may be the equivalent of a microphone pickup which provides an analog output signal corresponding to the magnitude of the airflow passed thereover. Accordingly, and in a preferred embodiment, airflow sensor 104 may be placed adjacent any airflow orifice in the body, and preferably on the patient's upper lip and below the nose.

The sensors 100, 102 and 104 are connected to a recorder 119 which can be taken home by a patient. Each of the sensors 100, 102 and 104 provide an analog signal to a corresponding signal processor apparatus. The analog signal from heart rate sensor 100 is applied to a heart rate signal processor 106. The analog signal from oxygen saturation sensor 102 is applied to oxygen saturation signal processor 108. Finally, the analog signal from airflow sensor 104 is applied to airflow signal processor 110. Signal processors 106 and 108 may be constructed in accordance with New Jr. et al., or an equivalent, which use the analog sensor input to obtain the heart rate and oxygen saturation, respectively, in analog form. Signal processor 110 may provide a proper impedance match and amplification for the airflow signal to the following stage.

The signals from signal processors 106, 108, and 110 may be provided to an analog-to-digital (A/D) converter 112. Analog-to-digital converter 112 may digitize the corresponding analog signals. The digital output of the three sensed signals of analog-to-digital converter 112 may be provided to a memory 118. It is contemplated that a digital clock generator 116 may be provided, which may provide a digital clock signal which correlates the digitized signals with time. Accordingly, digital clock generator 116 may provide a digital clock signal to memory 118 as shown. The preferred sample frequency for analog-to-digital converter 112 is approximately 10 Hertz, which is deemed sufficiently above the Nyquist rate of all frequencies of interest.

A computer 114 may be coupled to memory 118. Memory 118 has input and output capabilities which are compatible with the I/O interfaces of computer 114, and may be controlled by computer 114. In a preferred embodiment, data recorder 119 may be an OxiFlow® recorder, available from the assignee of the present invention. OxiFlow® recorder 119 may record all sensor data and program generated data, and may provide previously recorded data to computer 114.

In a preferred embodiment, computer 114 is an IBM compatible microprocessor having a 80386/20 or higher capability, a 1.44 Mb. floppy drive, a hard drive with at least 10 Mb of free disk space, at least 4 Mb of random access memory (RAM), an open serial and parallel port, Microsoft® Windows™ 3.1 or higher operating system, a graphics card and monitor 120 of at least 640×480 pixels and 16 shades of gray capability, a keyboard 122, a Microsoft-compatible mouse 124, and a Windows™ compatible printer 126.

Figure 2:
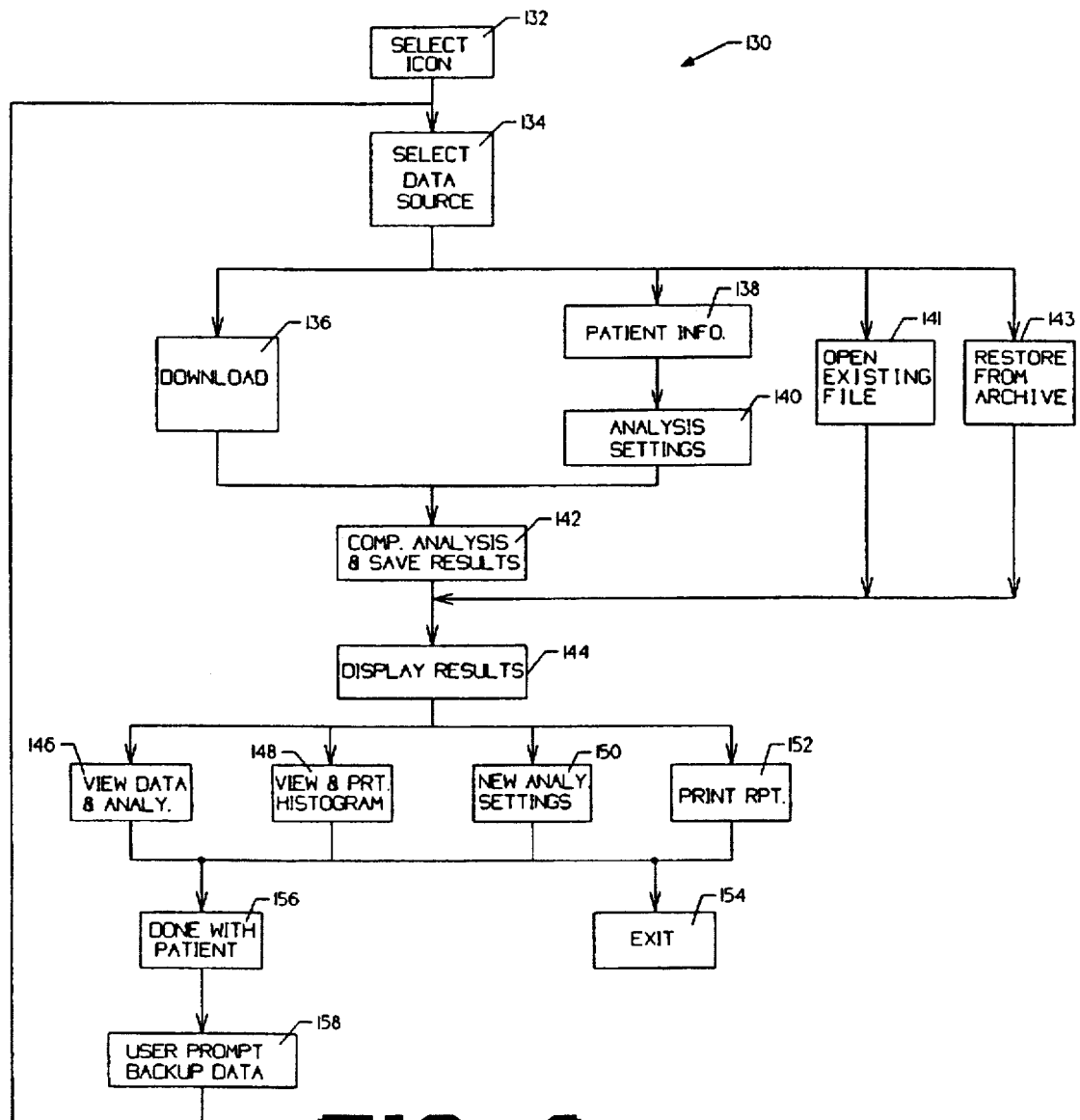
FIG. 2 is a flow diagram of an exemplary operator interaction with the system shown in FIG. 1.

FIG. 2 is a flow diagram of an exemplary operator interaction with the above described system 98. It is contemplated that present invention may be implemented in either hardware or software, or a combination thereof. In a preferred embodiment, computer 114 is programmed with a computer program written in the "C/CH" programming language to perform the desired functions thereof.

The general program flow is shown at 130. The operator uses keyboard 122 and/or mouse 124 as inputs to initiate and run the computer program interfaces. The outputs may be displayed on the screen of monitor 120, described above and shown later. In a preferred embodiment, conventional Windows™ procedures using the screen display on monitor 120 showing the various options, which are readily selected by the operator using mouse 124, provide the operator interactions. This provides operating ease with a minimum of training and takes advantage of the existing Windows™ operating system structure.

Figure 3:
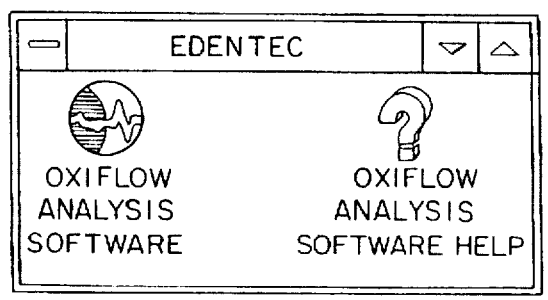
FIG. 3 shows an exemplary program icon in accordance with the present invention.

The program is called up using a program icon labeled "OxiFlow Analysis Software" which is displayed on monitor 120 in Windows™ format as one of the application program icons. FIG. 3 shows a preferred program icon in accordance with the present invention. Hereafter when the term screen is used this will be the screen on monitor 120. The operator merely "double-clicks" on the OxiFlow Analysis icon represented by Select Icon block 132 using the conventional Windows™ approach to call up the application program.

The screen called up by select icon block 132 has a title bar with "OxiFlow Analysis Software" as the heading in the conventional Windows™ format. Immediately below the title bar is a control bar with the conventional Windows™ hypertext words "File Setup View and Help" labels.

Figure 5:
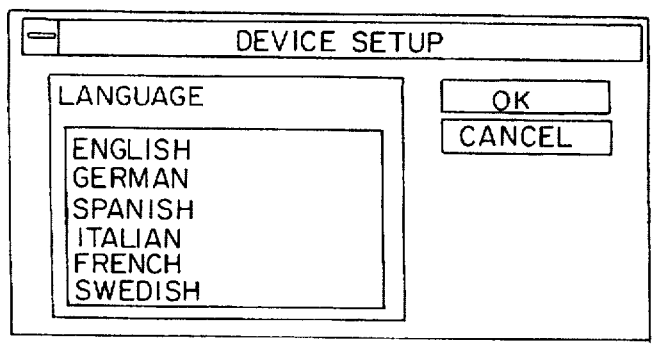
FIG. 5 shows an exemplary Device Setup menu in accordance with the present invention.

After selecting the OxiFlow Analysis icon 132, the user may select a data source as indicated by block 134. Clicking on Setup in the control bar of the "OxiFlow Analysis Software" window calls up a menu with Events, Patient Information and Recorder as options. Clicking on "Recorder" calls up a screen labeled "Device Setup" with a number of language options. FIG. 5 shows an exemplary Device Setup menu. Immediately below the control bar are three hypertext boxes respectively labeled "Data Source, Backup and Restore." Clicking on any hypertext words in the control bar or any of the hypertext boxes will call up the named functions.

Figure 6:
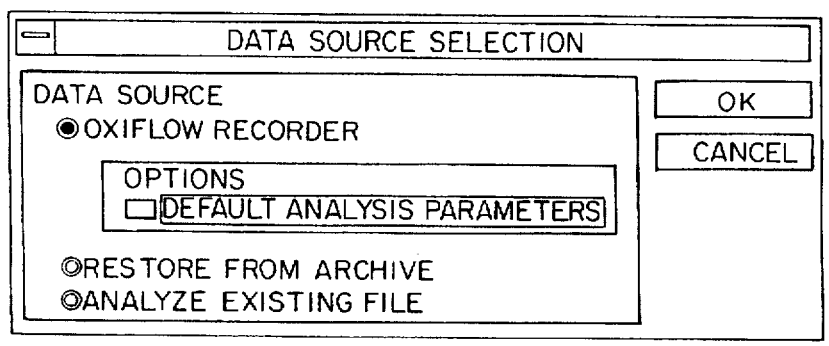
FIG. 6 shows an exemplary Data Source Selection menu in accordance with the present invention.
Figure 7:
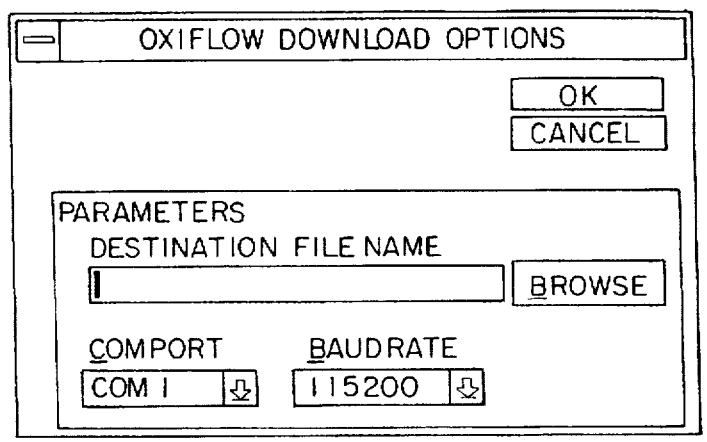
FIG. 7 shows an exemplary OxiFlow Download Options menu in accordance with the present invention.

Clicking on the "Data Source" hypertext box calls up a screen labeled "Data Source Selection", with the options of: OxiFlow Recording, Restore from Archives and Open Existing File. FIG. 6 shows an exemplary Data Source Selection menu. If the user selects the OxiFlow Recorder as the data source, an overlay screen labeled "OxiFlow Download Options" is displayed. FIG. 7 shows an exemplary OxiFlow Download Options menu. The user is prompted to provide a destination filename, the appropriate COM port, and the transfer baud rate. Once approved by clicking OK, the data is downloaded from memory 118, as indicated by Download block 136.

Figure 4:
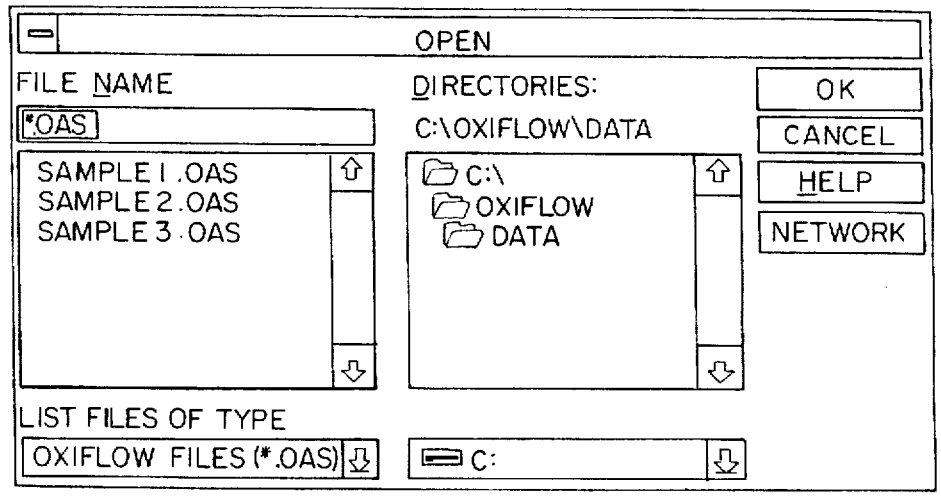
FIG. 4 shows an exemplary Open File menu in accordance with the present invention.

If the user selects an existing file on the hard drive of computer 114, an overlay screen labeled "Open" is called up. This screen has the provisions to provide the following information to the program: File Named, List Type of Files, Directories and Drive. FIG. 4 shows an exemplary File Open menu. Upon providing the data, or using the default parameters and clicking on OK, the file selected is retrieved, as indicated by the Download block 136.

Figure 8:
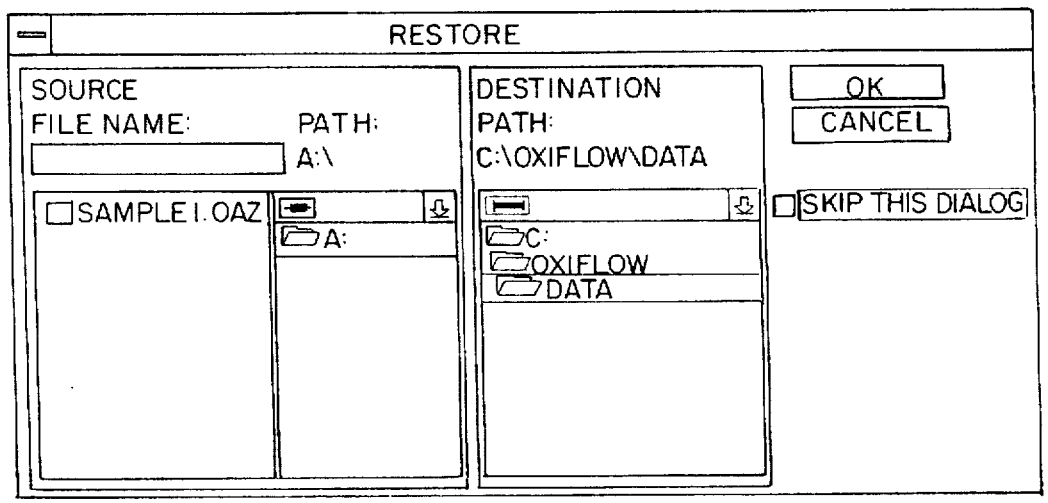
FIG. 8 shows an exemplary File Restore menu in accordance with the present invention.

If the user selects to restore a file from archive, an overlay screen labeled "Restore" is called up, with Source, Path and Destination options. FIG. 8 shows an exemplary Restore menu. Upon providing the data, or using the default parameters and clicking on OK, the data selected is retrieved, as indicated by the Download block 136.

During a download from the recorder, the data retrieval is performed in the background while the user is automatically prompted for patient information (see below), as indicated by the Patient Information block 138. FIG. 9 shows an exemplary Patient Information menu. The patient information menu allows each data set to be associated with a particular patient, and further provides relevant information for the proper diagnosis of sleep disorder including age, sex, etc.

Figure 10:
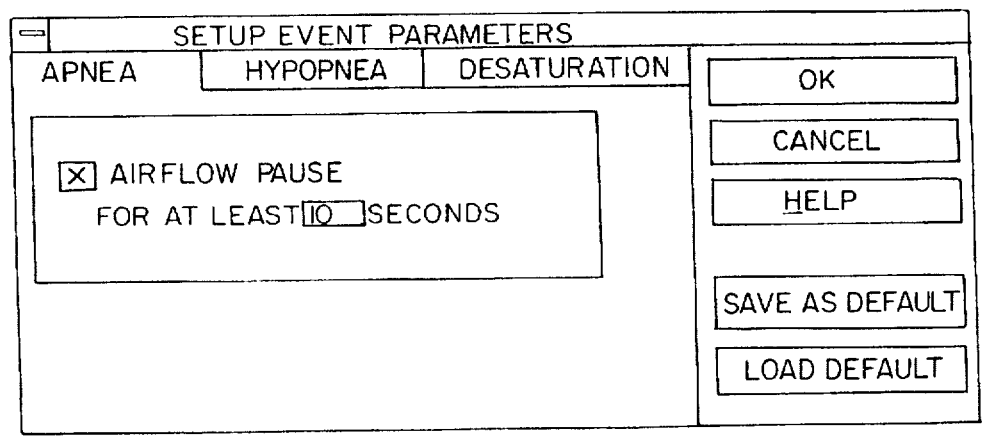
FIG. 10 shows an exemplary Setup Event Parameters menu for Apnea in accordance with the present invention.
Figure 11:
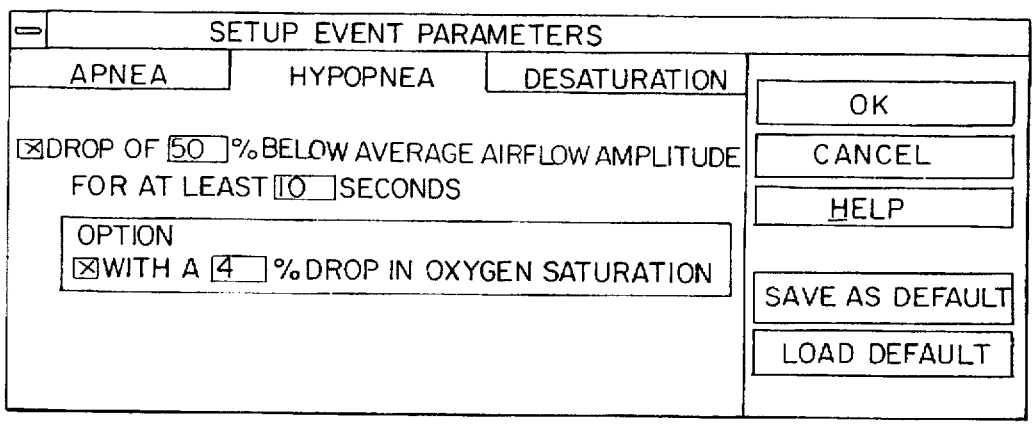
FIG. 11 shows an exemplary Setup Event Parameters menu for Hypopnea in accordance with the present invention.
Figure 12:
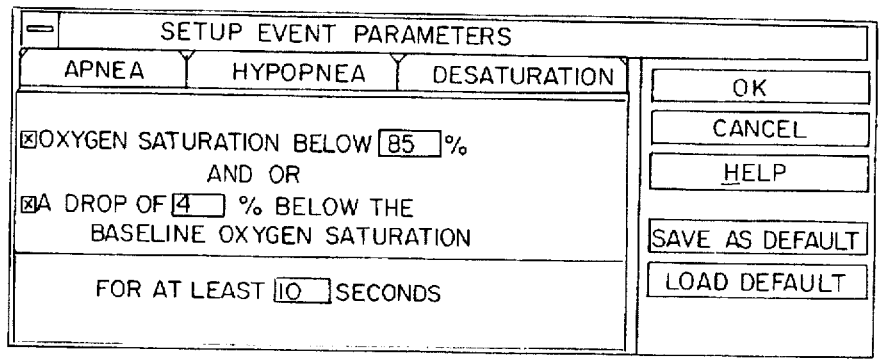
FIG. 12 shows an exemplary Setup Event Parameters menu for Desaturation in accordance with the present invention.

Once the patient information is entered at block 138, the analysis settings may be reviewed and changed if needed. The analysis settings may be changed via a number of "Setup Events Parameters" menus. An exemplary "Setup Event Parameters" menu for apnea parameters is shown in FIG. 10. An exemplary "Setup Event Parameters" menu for hypopnea parameters is shown in FIG. 11. Finally, an exemplary "Setup Event Parameters" menu for desaturation parameters is shown in FIG. 12.

With reference to the apnea parameters of FIG. 10, an airflow entry is displayed along with a dialog window for entering an apnea interval. If the system does not detect an airflow signal from airflow sensor 104, the X in the entry box immediately preceding "Airflow pause" is not displayed, and the above set-up prompt field will be skipped. The apnea interval entry has a default value of 10 seconds and can be set to an integer value within the range of 4 to 60 seconds, in the preferred mode, which specifies the minimum duration which constitutes an apnea event. The apnea detection algorithm itself is described with reference to FIG. 18.

With reference to the hypopnea parameters of FIG. 11, the top entry box must be set to "X" to enable hypopnea detection. If the "X" is not entered, hypopnea will not be detected. Further, hypopneas which overlap apneas will be discarded. The hypopnea menu allows the user to specify the percentage that the airflow must drop below an average (or baseline) airflow amplitude before a hypopnea event is detected. Coupled therewith, the hypopnea menu allows the user to specify the minimum time period that the airflow must drop below the average airflow amplitude before a hypopnea event is detected. Both of these conditions must be satisfied before a hypopnea event is reported.

The lower entry box controls whether hypopnea must be associated with a drop in oxygen saturation, with an entry of "X" indicating that such a drop must be included in the analysis. The oxygen saturation level must drop by the percentage specified below the baseline oxygen saturation level recorded at the start of the event. This integer field allows values in the range of 1 to 40% below the average (or baseline) airflow amplitude. Further, in a preferred embodiment, this drop in oxygen saturation must occur within 20 seconds of the end of the event. The hypopnea detection algorithm itself is described with reference to FIG. 18.

With reference to the desaturation parameters of FIG. 12, if no oxygen saturation signal is detected by the system, the desaturation menu will not be shown and the operation thereof will be disabled. The user may select either the top entry box, the bottom entry box, or both. If only the top entry box is selected, a fixed threshold will be used to determine desaturation. If only the bottom entry box is selected, a relative threshold will be used to determine desaturation. If both the top entry box and the bottom entry box are selected, then both fixed and relative threshold detections will be used. If neither the top entry box or the bottom entry box is selected, then desaturation detection will be disabled.

The "Oxygen saturation below_____%" field specifies the fixed threshold. In a preferred embodiment, this integer field allows values in the range of 60 to 100%. The initial default value is 85%. The "for at least _____ seconds" field specifies the minimum duration of a desaturation event in seconds. In a preferred embodiment, this integer field allows values in the range of 1 to 30 seconds. The initial default value is 10 seconds. If a fixed threshold is used, desaturation is defined as a drop in oxygen saturation below the specified percentage for a period of at least the specified seconds.

The "A drop of ___ % below the baseline oxygen saturation" field specifies the oxygen drop for a relative threshold. In a preferred embodiment, this integer field allows values in the range of 1 to 40%. The initial default value is 4%. If a relative threshold is used, desaturation is defined as a drop in oxygen saturation below the specified percentage of a baseline saturation level, for a period of at least the specified time period. The baseline calculation algorithm will be described below.

If both fixed and relative thresholds are selected, desaturation is defined as a drop in oxygen saturation below either the fixed threshold OR below the baseline oxygen saturation level. The oxygen saturation must remain below either threshold for a period of at least Time seconds.

In all cases, the oxygen saturation signal will be considered invalid if it is less than a predefined minimum of 61% oxygen. This will help eliminate desaturations due to low signals amplitudes and/or noise. Oxygen saturation levels will be included in the oxygen saturation histograms only if they are considered valid. The histogram algorithms are described below.

After the user has made the appropriate selections in the Setup Event Parameter menus, the data is retrieved via Download block 136, and the program automatically enters the Compute Analysis & Save Results block 142. A time bar shown on the monitor during the analysis indicates the progress, and after completion, the results are automatically saved. Note that new Analysis Settings 140 may be entered at any time by clicking on the Data Source hyperblock.

Figure 13:
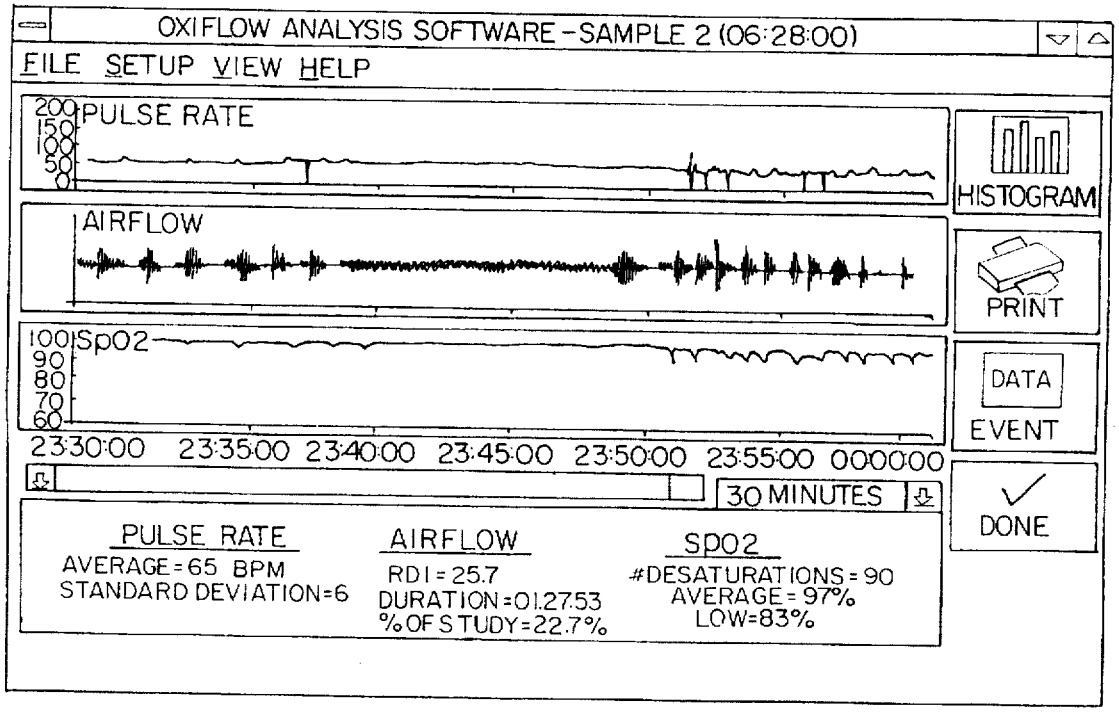
FIG. 13 shows an exemplary Analysis Display screen with three sensor outputs displayed.

After Compute Analysis & Save Results block 142 completes the required processing, the user may display the results of the analysis represented by Display Results block 144. The user may display results from previously existing files from the computer by Open Existing File block 141 or from an archive recording by Return From Archive block 143 (see FIG. 2). An exemplary screen for displaying the results is shown in FIG. 13.

A number of selections may be made while viewing the results of the analysis. For example, the user may view the analysis results as shown at 146, view and print histograms of the results as shown at 148, set new analysis settings as shown at 150, and/or print a report as shown at 152.

Figure 16:
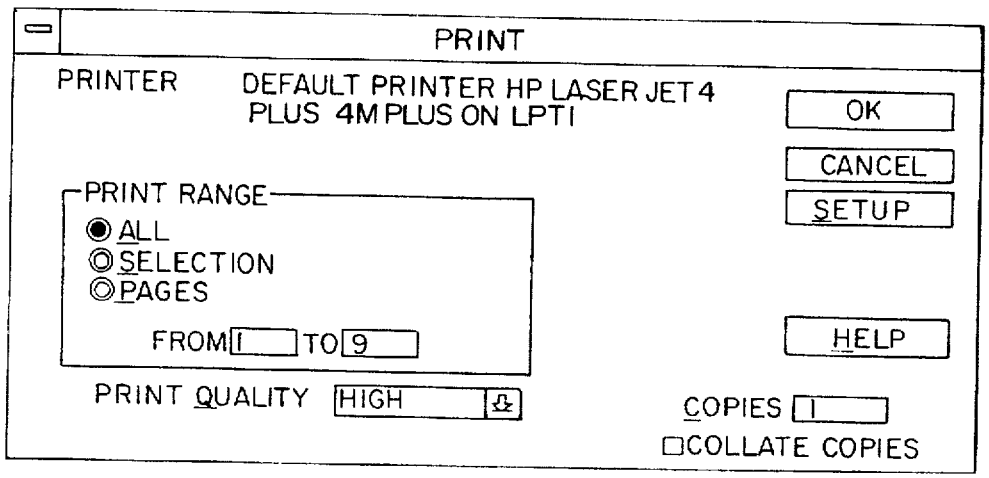
FIG. 16 shows an exemplary Print menu in accordance with the present invention.

With reference to the view block 146, a Zoom option may be used with 30 min., 1 Hr., 2 Hr., 4 Hr., and Total Duration selections. FIG. 14 shows an exemplary Time Interval drop down menu. Clicking on "Help" on the control bar calls up a table of contents. Using Help and About Help options providing assistance to the operator. With reference to the view and print histogram block 148, a histogram may be created from the data. FIG. 15 shows an exemplary histogram created by the program, showing both pulse rate and oxygen saturation. With reference to the new analysis settings block 150, the user may enter new analysis parameters as described above. Finally, with reference to print report block 152, the user may print various reports to printer 126. FIG. 16 shows an exemplary print menu.

Figure 17:
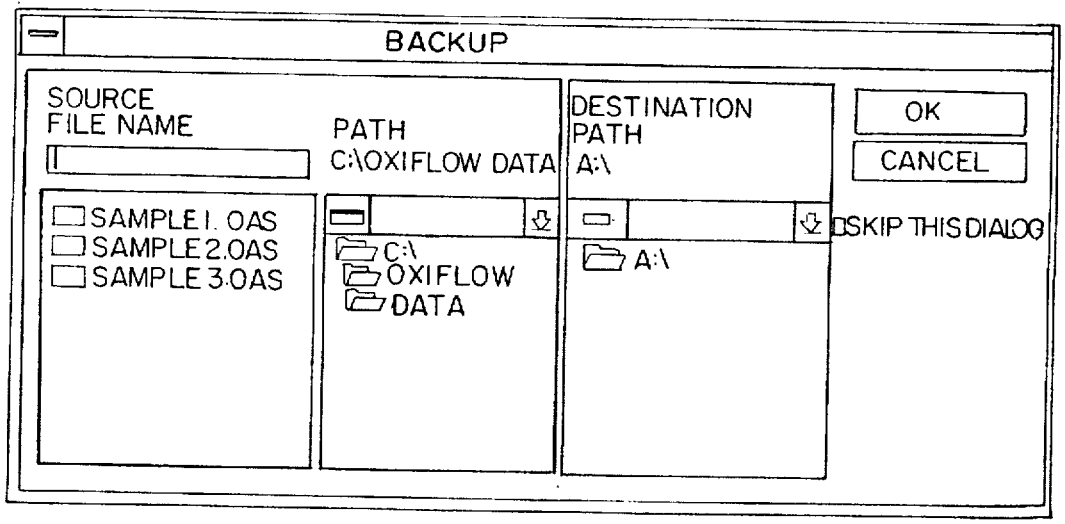
FIG. 17 shows an exemplary Backup menu in accordance with the present invention.

If the user wishes, the user may exit the program at this time as indicated by exit block 154. Alternatively, the user may wish to analyze another patients' records. If so, the user may indicate that data analysis is complete for the selected patient, as shown at block 156. The program may then prompt the user to backup the data for the selected patent as indicated at block 158. FIG. 17 shows an exemplary backup menu. The user may then select another data source via block 134 as described above.

Figure 18:
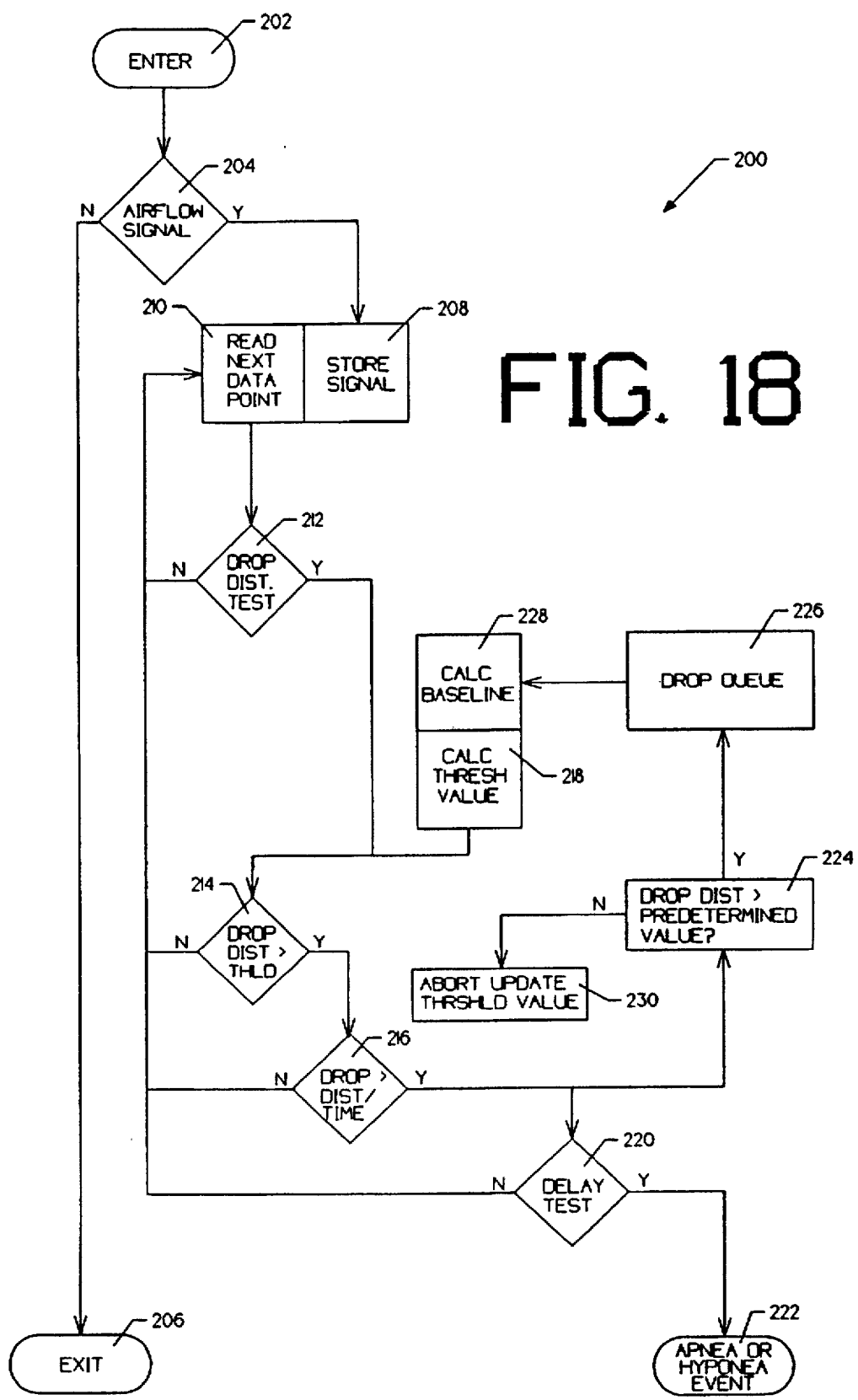
FIG. 18 is a flow diagram of an exemplary apnea-hypopnea algorithm.

FIG. 18 is a flow diagram showing exemplary apnea and hypopnea detection algorithms. The algorithm is executed in the Compute Analysis and Save Results block 142 or new analysis settings in block 150 of FIG. 2. In a preferred embodiment, the only difference between the apnea and hypopnea detection algorithms is the threshold testing values. This threshold difference will be described with reference to the threshold tests below.

Generally, both apnea and hypopnea detection is performed using only the digitized airflow signal. To search for an apnea event, the algorithm first searches for a valid peak of inspiration and a following start of inspiration. Then, the algorithm checks the time between the valid peak of inspiration and the following start of inspiration against a predefined apnea interval. If the time is greater than the predefined apnea interval, an apnea event is detected.

In a preferred embodiment, two conditions must be satisfied for a local maximum in the digitized airflow signal to be considered a valid peak of inspiration. The first condition is that a drop distance from the local maximum to the next local minimum must be greater than a predefined threshold value. The second condition is that the local maximum must drop at least a specified drop distance within a specified time period. These conditions help ensure that the local maximum is in fact a valid peak of inspiration.

Referring specifically to FIG. 18, the digitally converted airflow signal from airflow sensor 104 is accessed by Enter block 202 and passed to Airflow Signal block 204. Airflow Signal block 204 determines whether an airflow signal is present. If no airflow signal is present, control is passed to Exit block 206, wherein the algorithm is exited.

If an airflow signal is present, control is passed to store signal block 208. Store signal block 208 stores the digitized airflow sensor data points in a FIFO manner, which is the program equivalent of a push-down file.

Read Next Data Point block 210 reads the oldest data point in Store signal block 208 and provides the data point to Drop Distance Test block 212. A drop distance is defined as the difference in amplitude between a local maximum and the following local minimum. A valid drop distance is defined as the difference in amplitude of the digitized airflow signal from a valid peak of inspiration portion to a next succeeding end of expiration portion. Drop Distance Test Block 212 determines whether the current data point is a local minimum. Drop Distance Test Block 212 searches for local maximums and local minimums. The local minimum is stored to evaluate the drop distance of the subsequent local minimum. If the current data point is not a local minimum, control is passed back to block 210 wherein the next data point is read. If, however, the current data point is a local minimum, control is passed to Drop Distance Greater than Threshold block 214. Drop Distance Greater than Threshold block 214 and Drop Distance Greater than DIST/TIME block 216 collectively determine whether a local maximum is indeed a valid peak of inspiration.

As can readily be seen, the digitized airflow signal corresponds to the respiration of the patient and may have a number of successive start of inspiration portions, peak of inspiration portions, expiration portions, and end of expiration portions. The term inspiration is used to designate when the patient is breathing into the body while the term expiration is used to designate when the patient is breathing out of the body. Accordingly, a peak of inspiration portion corresponds to the point where the patient has completed a breath into the body, while an end of expiration portion corresponds to the point wherein the patient has completed a breath out of the body. Similarly, a start of inspiration portion corresponds to the point where the patient begins a breath into the body, while a start of expiration corresponds to the point where the patient begins a breath out of the body.

It is recognized that the digitized airflow signal may have a number of local maximums and local minimums wherein each of the number of local maximums and local minimums have a corresponding amplitude. Some of the local maximums are valid, while others are due to non-monatomic breathing or noise. Thus, each of the number of peak of inspiration portions may correspond to one of the number of local maximums, but not necessarily vice-versa. It is contemplated that Drop Distance Greater than Threshold block 214 and Drop Distance Greater than DIST/TIME block 216 may collectively determine which of the number of peak of inspiration portions are indeed valid.

In a preferred embodiment, Drop Distance Greater than Threshold block 214 and Drop Distance Greater than DIST/TIME block 216 determine that a local maximum is a valid peak of inspiration if: the amplitude of the local maximum exceeds the amplitude of the following local minimum by a predetermined threshold value; and the amplitude of the local maximum drops by a predetermined amount within a predetermined time period.

Accordingly, Drop Distance Greater than Threshold block 214 determines whether the amplitude of the local maximum exceeds the amplitude of the following local minimum by a predetermined threshold value. The predetermined threshold value is provided by Calculate Threshold Value block 218, which is described in more detail below.

If the amplitude of the local maximum does not exceed the amplitude of the following local minimum by a predetermined threshold value, control is passed back to block 210 wherein the next data point is read. If the amplitude of the local maximum exceeds the amplitude of the subsequent local minimum by a predetermined threshold value, control is passed to Drop Distance Greater than DIST/TIME block 216.

Drop Distance Greater than DIST/TIME block 216 determines whether the amplitude of the local maximum drops by a predetermined amount within a predetermined time period. It is contemplated that this may require keeping a queue of values over a full airflow period, i.e. between successive "peaks". The predetermined amount may be simply a percentage of the threshold used in Drop Distance Greater than Threshold block 214. In a preferred embodiment, the predetermined amount is 15% of the threshold used in Drop Distance Greater than Threshold block 214. Further, in a preferred embodiment, the predetermined time period is set to 1.4 seconds, but may be user definable. For example, this time period can be defined as the average of the highest 10 of the previous 50 valid time periods or a minimum value of 1.4 seconds, whichever is greater. A time period can be measured from the local maximum to the subsequent local minimum.

If the amplitude of the local maximum has not dropped the predetermined amount within the predetermined time period, control is passed back to block 210 wherein the next data point is read. If the amplitude of the local maximum has dropped by the predetermined amount within the predetermined time period, the local maximum is deemed a VALID peak of inspiration.

Once a valid peak of inspiration has been identified, control is passed to Delay Test block 220. Delay Test block 220 determines if the delay in respiration exceeds an predetermined apnea interval. The apnea interval may be defined as the time between a valid peak of inspiration portion and the next succeeding start of inspiration portion. If the time from the valid peak of inspiration portion to the next succeeding start of inspiration portion is less then the apnea interval, control is passed back to block 210 wherein the next data point is read. If however, the time from the valid peak of inspiration portion to the next succeeding start of inspiration portion is greater than or equal to the apnea interval, an apnea or hypopnea event is detected, depending upon the threshold used as described below. This information may be stored for summary and display.

The value of the threshold used by Drop Distance Greater Than Threshold block 214 is provided via blocks 224, 226, 228, 218, and 230. Drop Distance Greater Than DIST/TIME block 216 may provide the valid peak of inspiration portion to Drop Distance Greater Than a Predetermined Value block 224. Drop Distance Greater Than a Predetermined Value block 224 may compare the drop distance of the valid peak of inspiration portion with a predetermined minimum threshold. If the drop distance of the valid peak of inspiration signal is less than the predetermined minimum threshold, control is passed to element 230 and the threshold update algorithm is aborted. However, if the drop distance of the valid peak of inspiration signal is greater than the predetermined minimum threshold, the drop distance is provided to Drop Queue 226. Drop Queue 226 may store, in a FIFO manner, the "IN" most recent drop distances of valid peak of inspiration portions. The drop queue may be coupled to Calculate Baseline block 228.

Calculate Baseline block 228 may use the drop distances in Drop Queue 226 to determine a baseline amplitude for calculating a subsequent valid peak of inspiration. That is, the predetermined threshold value used to determine if a peak of inspiration is valid may be set to a percentage of the baseline amplitude wherein the baseline amplitude is defined as the average of the second through the sixth highest valid drops in a drop queue of size 10. The highest valid drop is removed to eliminate breaths which may be atypical of the normal breathing pattern (i.e., a large sigh). The lowest breaths are removed to eliminate the effect of abnormal breathing patterns on the baseline and thereby being able to continue to detect an abnormal breathing pattern (i.e., hypopnea).

Calculate threshold value block 218 may determine the threshold used by Drop Distance Greater Than Threshold block 214 by calculating a percentage of the baseline amplitude. For apnea detection, and in a preferred embodiment, Calculate Threshold Value block 218 calculates the threshold value by taking 20% of the baseline value calculated in block 228. For hypopnea detection, this threshold value is set to (100-PCT)% of the baseline amplitude, where PCT was the value previously specified by the operator. In a preferred embodiment, this is the only difference between the apnea and the hypopnea detection algorithms. These values are used for the respective apnea and hypopnea detection tests of block 214.

Optionally, for hypopnea detection, the system may include an oxygen sensor coupled to the patient for providing a time varying oxygen saturation signal to the input means thereby resulting in a digitized oxygen saturation signal. The system may determine if the oxygen saturation level falls below a predetermined oxygen saturation level for a predetermined time period. If an apnea event is detected under these conditions, and optionally if the oxygen saturation level drops below the predetermined oxygen level for the predetermined time period, a hypopnea event is detected.

Figure 19:
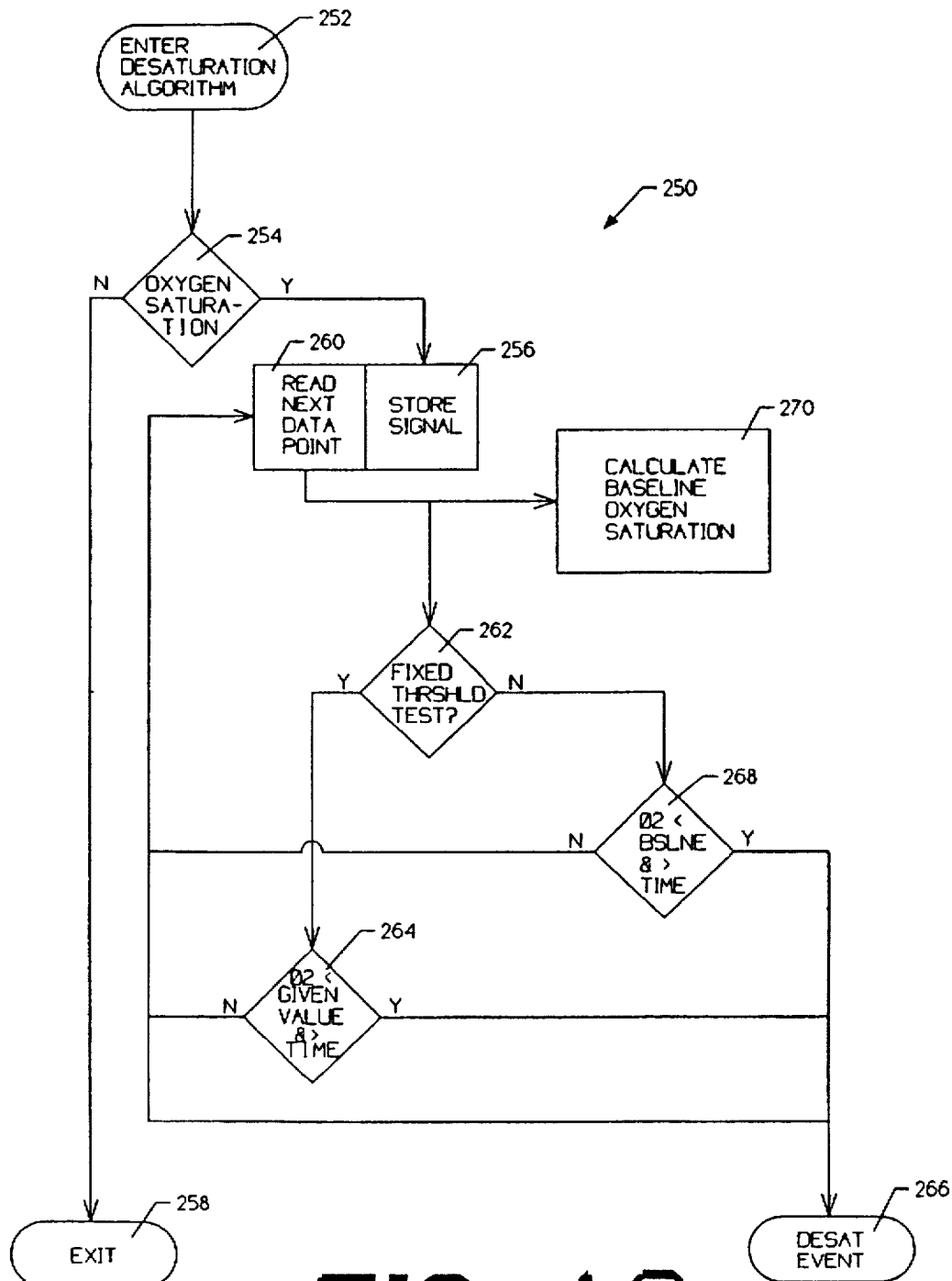
FIG. 19 is a flow diagram of an exemplary desaturation algorithm.

FIG. 19 is a flow diagram of an exemplary desaturation algorithm. The oxygen desaturation algorithm is generally shown at 250. The oxygen saturation signal from oxygen saturation sensor 102 is entered into the Enter Desaturation Algorithm block 252 and passed along to oxygen saturation Signal Detection block 254 which determines if a digitized airflow signal is present. If no airflow signal is present, control is passed to Exit block 258.

If an oxygen saturation signal is present, control is passed to Store Signal block 256. Store Signal block 256 stores the digitized oxygen saturation sensor data points in a FIFO manner, which is the program equivalent of a push-down file. Control is then passed to Read Next Data Point block 260.

Read Next Data Point block 260 reads the oldest data point and provides the data point to Fixed Threshold Test block 262. Fixed Threshold Test block 262 determines whether a fixed threshold has been selected by the user and/or whether a relative threshold has been selected. If the user selected both a fixed threshold test and a relative threshold test, both tests are executed concurrently.

In any event, if the fixed threshold test is selected, control is passed to block 264. Block 264 compares the digitized oxygen saturation against a predefined fixed oxygen saturation threshold. The fixed oxygen saturation threshold is specified by the user, as described with reference to FIG. 12. If the digitized oxygen saturation remains below the predefined fixed threshold for the predefined period of time, control is passed to Desaturation Event block 266, wherein a desaturation event is detected. If the digitized oxygen saturation level does not remain below the predefined fixed threshold for the predefined period of time, control is passed to Read Next Data Point block 260 wherein the next data point is read.

If the relative threshold test is selected, control is passed from block 262 to block 268. For this test, the oxygen saturation must be below a baseline oxygen saturation threshold for greater than a predefined time, as specified by the user with reference to FIG. 12.

The baseline oxygen saturation threshold may be defined as follows. A baseline time interval may be broken into "N" time windows, and an average oxygen level may be computed for each time window. The baseline oxygen saturation threshold may then be computed by averaging the highest "M" average oxygen levels for each of the "N" time windows, wherein M is less than N. To prohibit invalid signals from effecting the results, it is contemplated that any time window that has an invalid oxygen level therein may not be selected as one of the highest M oxygen levels.

For example, Baseline Oxygen Saturation block 270 may calculate oxygen baseline as follows: 1) split the previous five minutes into five second windows; 2) find the highest oxygen value in each of the windows; 3) determine the highest 10 values found in 2) above; and 4) average of the 10 values found in 3) is the baseline. The baseline oxygen saturation level used in this calculation may thus be updated every 5 seconds by dividing a 5 minute interval into 60 windows of 5 second duration.

If block 268 determines that the oxygen saturation level remains below the baseline oxygen saturation threshold for the predefined time period, a desaturation event is detected and control is passed to Desaturation Event block 260. If, however, block 268 determines that the oxygen saturation level does not remain below the baseline oxygen saturation threshold for the predefined time period, control is passed back to Read Next Data Point block 260 wherein the next data point is read.

Finally, it is contemplated that the above referenced system may include a pulse sensor coupled to the patient for providing a time varying heart pulse signal to the input means, thereby resulting in a digitized pulse signal. The system may determine the pulse rate of the patient, and correlate the pulse rate with the respiration and oxygen saturation signals. This may help a clinician diagnose the sleep events.

As can readily be seen, the present invention provides a sophisticated analysis of sensed airflow, pulse rate and oxygen saturation from a patient to analyze, score, display and record the apnea, hypopnea and desaturation of the patient using a minimum of specialized apparatus and programs. This system uses the extensive capabilities of a modern microprocessor and its operating system to the fullest along with the specialized equipment and program in providing this capability.

The method of prompting the appropriate operator response based upon the Windows™ operating system permits using a number of routes to arrive at the prompt menu with equivalent operating results. The use of different menus, menu access, different display formats, or algorithm criteria is obvious to one skilled in current microprocessor and microprocessor control system art.

Having thus described the preferred embodiments of the present invention, those of skill in the art will readily appreciate that the teachings found herein may be applied to yet other embodiments within the scope of the claims hereto attached.

What is claimed is:

1. A system for analyzing patient airflow to determine and score abnormal sleep events, comprising:

at least one sensor for sensing the airflow of a patient;

input means for receiving a time varying analog airflow signal from the at least one sensor wherein the analog airflow signal corresponds to the respiration of the patient and has a number of successive start of inspiration portions, peak of inspiration portions, expiration portions, and end of expiration portions; said input means digitizing the analog airflow signal thereby providing a digitized airflow signal;

clock means for providing a digital clock signal to correlate the digitized airflow signal with time;

receiving means for receiving the digitized airflow signal and the digital clock signal;

determining means, coupled to said receiving means, for determining a delay in the respiration of the patient; and wherein said determining means determines the portions of the digitized airflow signal that correspond to the successive peak of inspiration portions and the corresponding successive start of inspiration portions, wherein an apnea interval is defined as the time between a valid peak of inspiration portion and the next succeeding start of inspiration portion; said determining means determining which of the number of apnea intervals are longer than a predetermined apnea threshold, thereby indicating an apnea event.

2. A system according to claim 1 further comprising storing means for storing the digitized airflow signal and the digital clock signal for later display and analysis.

3. A system according to claim 1 wherein the digitized airflow signal has a number of local maximums and local minimums wherein each of the number of local maximums and local minimums have a corresponding amplitude, each of the number of peak of inspiration portions corresponding to one of the number of local maximums, said determining means determining which of the number of peak of inspiration portions are valid peak of inspiration portions.

4. A system according to claim 3 wherein said determining means determines that a particular peak of inspiration portion is valid if:

i. the amplitude of the local maximum corresponding to the particular peak of inspiration portion exceeds the amplitude of the subsequent local minimum by a predetermined threshold value; and ii. the amplitude of the local maximum corresponding to the particular peak of inspiration portion drops by a predetermined amount within a predetermined time period.

5. A system according to claim 4 wherein a valid drop distance is defined as the difference in amplitude of the digitized airflow signal from a valid peak of inspiration portion to a next succeeding end of expiration portion, said system further comprising a drop queue for storing in a FIFO manner the "N" most recent valid drop distances.

6. A system according to claim 5 wherein said predetermined threshold value is set at a percentage of a baseline amplitude wherein the baseline amplitude is defined as the average of the second through the sixth highest valid drops in a drop queue of size 10; the highest valid drop is removed to eliminate breaths which may be atypical of the normal breathing pattern; and the lowest breaths are removed to eliminate the effect of abnormal breathing patterns on the baseline and thereby being able to continue to detect an abnormal breathing pattern.

7. A system according to claim 5 wherein said valid drop distance must be greater than a predetermined amount before the valid drop distance is stored in the drop queue.

8. A system according to claim 5 wherein said predetermined amount is set to a percentage of the predetermined threshold value.

9. A system according to claim 1, further comprising means for inputting a user defined predetermined apnea threshold.

10. A system according to claim 1 further comprising an oxygen sensor and means for coupling the oxygen sensor to the patient for providing a time varying oxygen saturation signal to said input means thereby resulting in a digitized oxygen saturation signal, said determining means determining if the oxygen saturation level falls below a predetermined oxygen level for a predetermined time period.

11. A system according to claim 10 wherein said predetermined oxygen level is defined as a percentage of a baseline threshold.

12. A system according to claim 11 wherein a baseline time interval is broken into "N" time windows, wherein an average oxygen level is computed for each time window, the baseline threshold is computed by averaging the highest "M" oxygen levels for the "N" time windows, wherein M is less than N.

13. A system according to claim 12 wherein any time window that has an invalid oxygen level therein is not selected as one of the highest M oxygen levels.

14. A system according to claim 1 further comprising a pulse sensor coupled to the patient for providing a time varying heart pulse signal to said input means thereby resulting in a digitized pulse signal, said determining means determining the pulse rate of the patient.

15. A system according to claim 1 wherein said determining means comprises a processor.

16. A system according to claim 15 wherein said processor is a standard programmable personal computer.

17. A method for analyzing patient airflow to determine and score abnormal sleep events, comprising the steps of:

inputing a time varying analog airflow signal from at least one sensor that is sensing the airflow of a patient wherein the analog airflow signal corresponds to the respiration of the patient and has a number of successive start of inspiration portions, peak of inspiration portions, expiration portions, and end of expiration portions; said inputing step digitizing the analog airflow signal thereby providing a digitized airflow signal;

providing a digital clock signal to correlate the digitized airflow signal with time;

receiving the digitized airflow signal and the digital clock signal;

determining the respiration of the patient from the digitized airflow signal by determining a delay in the respiration of the patient; and wherein said determining step determines the portions of the digitized airflow signal that correspond to the successive peak of inspiration portions and the corresponding successive start of inspiration portions, wherein an apnea interval is defined as the time between a valid peak of inspiration portion and the next succeeding start of inspiration portion; said determining step determining which of the number of apnea intervals are longer than a predetermined apnea threshold, thereby indicating an apnea event.

18. A system according to claim 17 wherein the digitized airflow signal has a number of local maximums and local minimums wherein each of the number of local maximums and local minimums have a corresponding amplitude, each of the number of peak of inspiration portions corresponding to one of the number of local maximums, said determining step determining which of the number of peak of inspiration portions are valid peak of inspiration portions.

19. A system according to claim 18 wherein said determining step determines that a particular peak of inspiration portion is valid if:

i. the amplitude of the local maximum corresponding to the particular peak of inspiration portion exceeds the amplitude of the subsequent local minimum by a predetermined threshold value; and ii. the amplitude of the local maximum corresponding to the particular peak of inspiration portion drops by a predetermined amount within a predetermined time period.

20. A system according to claim 19 wherein said predetermined threshold value is set at a percentage of a baseline amplitude wherein the baseline amplitude is defined as the average of the second through the sixth highest valid drops in a drop queue of size 10; the highest valid drop is removed to eliminate breaths which may be atypical of the normal breathing pattern; and the lowest breaths are removed to eliminate the effect of abnormal breathing patterns on the baseline and thereby being able to continue to detect an abnormal breathing pattern.

21. A system according to claim 20 wherein said predetermined amount is set to a percentage of the predetermined threshold value.

22. A method according to claim 17 wherein an oxygen sensor is provided such that said oxygen sensor is coupled to the patient for providing a time varying oxygen saturation signal to said inputing step thereby resulting in a digitized oxygen saturation signal, said determining step determining if the oxygen saturation level falls below a predetermined oxygen level for a predetermined time period.

23. A method according to claim 22 wherein said predetermined oxygen level is defined as a percentage of a baseline threshold.

24. A method according to claim 23 wherein a baseline time interval is broken into "N" time windows, wherein an average oxygen level is computed for each time window, the baseline threshold is computed by averaging the highest "M" oxygen levels for the "N" time windows, wherein M is less than N.

25. A method according to claim 24 wherein any time window that has an invalid oxygen level therein is not selected as one of the highest M oxygen levels.

26. A method according to claim 17 wherein a pulse sensor is provided wherein said pulse sensor is coupled to the patient for providing a time varying heart pulse signal to said inputing step thereby resulting in a digitized pulse signal, said determining step determining the pulse rate of the patient.

* * * * *